(12) United States Patent
Kim (10) Patent No.: US 10,463,400 B2
(45) Date of Patent: Nov. 5, 2019

(54) BONE SURGICAL APPARATUS WITH RATCHETING FUNCTION

(71) Applicant: THE GENERAL HOSPITAL CORPORATION, Boston, MA (US)

(72) Inventor: Saechin Kim, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/121,720

(22) PCT Filed: Mar. 2, 2015

(86) PCT No.: PCT/US2015/018238
§ 371 (c)(1),
(2) Date: Aug. 25, 2016

(87) PCT Pub. No.: WO2015/131173
PCT Pub. Date: Sep. 3, 2015

(65) Prior Publication Data
US 2016/0374728 A1     Dec. 29, 2016

Related U.S. Application Data

(60) Provisional application No. 61/946,350, filed on Feb. 28, 2014.

(51) Int. Cl.
*A61B 17/70*     (2006.01)
*A61B 17/68*     (2006.01)

(52) U.S. Cl.
CPC ...... *A61B 17/7023* (2013.01); *A61B 17/7011* (2013.01); *A61B 17/7013* (2013.01); *A61B 17/7032* (2013.01); *A61B 2017/681* (2013.01)

(58) Field of Classification Search
CPC .................. A61B 17/7014–17/7017
(Continued)

(56) References Cited

U.S. PATENT DOCUMENTS

| 5,242,646 A | 9/1993 | Torigoe et al. |
| 5,928,231 A | 7/1999 | Klein et al. |

(Continued)

FOREIGN PATENT DOCUMENTS

| WO | 2009146377 A1 | 12/2009 |
| WO | 2011112748 A2 | 9/2011 |
| WO | WO2011112748 | 9/2011 |

OTHER PUBLICATIONS

International Search Report and Written Opinion for international patent application No. PCT/US2015/018238, dated Jun. 10, 2015.

*Primary Examiner* — Nicholas J Plionis
(74) *Attorney, Agent, or Firm* — Quarles & Brady LLP (57) ABSTRACT

The present invention provides a bone surgical apparatus that includes a unit with a first end and an opposed second end. The first end of the unit includes a female component with an interior dimension and the second end includes a male component having exterior dimension. The female component and the male component are capable of mating. At least one of the female and male components also includes an adjustment mechanism with a first position that allows the component to rotate in a both a first rotational direction and a second rotational direction opposed to the first rotational direction, and a second position that prevents rotation of the component in the second rotational direction.

18 Claims, 7 Drawing Sheets

(58) Field of Classification Search
USPC .................................................. 606/256–259
See application file for complete search history.

(56) References Cited

U.S. PATENT DOCUMENTS

| | | | |
|---|---|---|---|
| 7,544,208 | B1 | 6/2009 | Mueller et al. |
| 7,587,961 | B1 | 9/2009 | Chiang |
| 2002/0193794 | A1* | 12/2002 | Taylor ................ A61B 17/7037 606/278 |
| 2006/0195095 | A1 | 8/2006 | Mueller et al. |
| 2007/0049936 | A1 | 3/2007 | Colleran et al. |
| 2007/0299448 | A1 | 12/2007 | Chin et al. |
| 2008/0015577 | A1 | 1/2008 | Loeb et al. |
| 2009/0118765 | A1 | 5/2009 | Mueller et al. |
| 2009/0204156 | A1 | 8/2009 | McClintock et al. |
| 2010/0042157 | A1 | 2/2010 | Trieu |
| 2010/0211105 | A1 | 8/2010 | Moumene et al. |
| 2011/0251646 | A1* | 10/2011 | Karnezis ............ A61B 17/7007 606/278 |
| 2013/0268006 | A1 | 10/2013 | Garamszegi |
| 2013/0282064 | A1* | 10/2013 | Arnin ................ A61B 17/7014 606/258 |

* cited by examiner

BONE SURGICAL APPARATUS WITH RATCHETING FUNCTION

CROSS-REFERENCE TO RELATED APPLICATIONS

This application represents the national stage entry of PCT International Application No. PCT/US2015/018238 filed Mar. 2, 2015, which claims the benefit of U.S. Provisional Patent Application Ser. No. 61/946,350 filed on Feb. 28, 2014 and entitled "BONE SURGICAL APPRATUS WITH RATCHETING FUNCTION."

STATEMENT REGARDING FEDERALLY SPONSORED RESEARCH

Not Applicable.

FIELD OF THE INVENTION

This invention relates to spinal surgery and associated apparatus.

BACKGROUND OF THE INVENTION

Spinal surgery for spinal deformities, such as scoliosis and kyphosis, is often performed on children who have not finished growing. Traditionally, the correction is achieved by a combination of techniques including distraction/compression along the axis of a rod, rotation/bending of the rod that is provisionally tethered to the spine, rotation of the spine around the rod, and pulling the spine to match a preconfigured rod. These technologies mostly focus on distraction along the longitudinal axis and/or use of a pre-contoured rod to change the shape of the curve of the spine.

In addition to the manipulation of the spine with hardware, many scoliosis and kyphosis procedures also involve spinal fusion. A goal of such procedures is to fuse as few vertebral levels as possible to preserve as much motion as possible while not jeopardizing the long term stability of the spine. Accordingly, it may be useful to provide a system and method to correct the curvature of the spine without the need for fusion.

Furthermore, due to the normal ongoing growth of the patient, it is sometimes necessary to perform repeat surgeries. For example, treatment of conditions such as scoliosis sometimes requires that previously implanted spinal hardware be adjusted in terms of its anchoring or shape so that treatment can be performed in a gradual manner. Even though the follow-up surgeries may be less traumatic than the original surgery that initially implanted the hardware, it may be beneficial for the patient if such surgeries could be minimized or even avoided altogether.

Therefore, what is needed is a method and apparatus to manipulate the curvature of the spine that reduces or eliminates both the need for repeat surgeries, the need for spinal fusion, or a combination thereof.

SUMMARY OF THE INVENTION

According to one embodiment, the present disclosure provides a bone surgical apparatus for manipulating a curvature of a spine. The bone surgical apparatus includes a unit having a first end and an opposed second end, the first end including a female component having an interior dimension, and the second end including a male component having an exterior dimension of a mating size to the interior dimension of the female component. The bone surgical apparatus further includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction.

In one aspect, the adjustment mechanism further includes a third position that prevents rotation of the one of the female component and the male component in both the first rotational direction and the second rotational direction.

In another aspect, the adjustment mechanism further includes a ratchet to control motion in one of the first rotational direction and the second rotational direction.

In yet another aspect, the adjustment mechanism further includes a ratchet to control motion in both of the first rotational direction and the second rotational direction.

In still another aspect, the bone surgical apparatus further includes a connector positioned between and coupled to the first end and the second end of the apparatus, and a pedicle screw configured to attach to a vertebra and receive the connector.

In a further aspect, the bone surgical apparatus further includes a bumper plate positioned on one of the first end and second the end. The bumper plate is configured to limit rotation of the bone surgical apparatus with respect to one of the first end and the second end.

In another aspect, the bone surgical apparatus further includes a selector for selecting between the first position and the second position.

According to another embodiment, the present disclosure provides a method of treating an abnormally shaped spine in a patient, the spine having a concave portion and an opposed convex portion. The method includes surgically implanting a bone surgical apparatus into the patient adjacent the convex portion of the spine, the bone surgical apparatus allowing rotation in a first rotational direction but at least selectively preventing rotation in an opposed second rotational direction.

In one aspect, the bone surgical apparatus includes a unit having a first end and an opposed second end, the first end including a female component having an interior dimension, and the second end including a male component having an exterior dimension of a mating size to the interior dimension of the female component, and an adjustment mechanism having a first position that allows one of the female component and the male component to rotate in both a first rotational direction and a second rotational direction opposed to the first rotational direction, and a second position that prevents rotation of the one of the female component and the male component in the second rotational direction.

In another aspect, the adjustment mechanism further includes a third position that prevents rotation of one of the female component and the male component in both the first rotational direction and the second rotational direction.

In yet another aspect, the adjustment mechanism further includes a ratchet to control motion in one of the first rotational direction and the second rotational direction.

In still another aspect, the adjustment mechanism further includes a ratchet to control motion in both the first rotational direction and the second rotational direction.

In a further aspect, the bone surgical apparatus further includes a connector positioned between and coupled to the first end and the second end of the apparatus, and a pedicle screw configured to attach to a vertebra and receive the connector.

In one aspect, the bone surgical apparatus further includes a bumper plate positioned on one of the first end and the second end. The bumper plate is configured to limit rotation of the bone surgical apparatus with respect to one of the first end and the second end.

In yet another aspect, the bone surgical apparatus further includes a feature for selecting between the first position and the second position.

In a further aspect, the manipulating step includes positioning a patient's body.

In one aspect, the manipulating step comprises positioning a magnet proximal the member.

In another aspect, the method treats scoliosis.

In yet another aspect, the method treats kyphosis.

According to yet another embodiment, the present disclosure provides a method for fusing a first bone and a second adjacent bone. The method includes attaching a first unit of a bone surgical apparatus to the first bone, attaching a second unit of the bone surgical apparatus to the second bone, wherein the bone surgical apparatus allows rotation of the first unit with respect to the second unit in one rotational direction but at least selectively prevents rotation in an opposed direction, rotating the first unit with respect to the second unit in the one rotational direction, and allowing the first bone and the second bone to fuse.

In one aspect, the first bone is a first vertebra and the second bone is a second vertebra.

In another aspect, the first unit has a first end including a female component with an interior dimension, and the second unit has a second end including a male component having an exterior dimension of a mating size to the interior dimension of the female component, and the bone surgical apparatus further includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction.

In yet another aspect, the adjustment mechanism further includes a third position that prevents rotation of one of the female component and the male component in both the first rotational direction and the second rotational direction.

In a further aspect, the adjustment mechanism further includes a ratchet to control motion in one of the first rotational direction and the second rotational direction.

In still another aspect, the adjustment mechanism further includes a ratchet to control motion in both the first rotational direction and the second rotational direction.

In one aspect, the first unit is attached to the first bone using a first pedicle screw, and the second unit is attached to the second bone using a second pedicle screw.

According to still another embodiment, the present disclosure provides a kit for treating an abnormally shaped spine in a patient. The kit includes a first unit having a first end including a female component with an interior dimension, and a second unit having a second end including a male component having an exterior dimension of a mating size to the interior dimension of the female component. At least one of the first unit and the second unit includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction.

In one aspect, the adjustment mechanism further includes a third position that prevents rotation of one of the female component and the male component in both the first rotational direction and the second rotational direction.

In another aspect, the adjustment mechanism further includes a ratchet to control motion in one of the first rotational direction and the second rotational direction.

In yet another aspect, the adjustment mechanism further includes a ratchet to control motion in both the first rotational direction and the second rotational direction.

In a further aspect, the kit further includes screws for attaching the first unit to a first vertebra and for attaching the second unit to a second vertebra.

According to a further embodiment, the present disclosure provides a kit for fusing a first bone and a second adjacent bone in a patient. The kit includes a first unit having a first end including a female component with an interior dimension, and a second unit having a second end including a male component having an exterior dimension of a mating size to the interior dimension of the female component. At least one of the first unit and the second unit includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction.

In one aspect, the adjustment mechanism further includes a third position that prevents rotation of one of the female component and the male component in both the first rotational direction and the second rotational direction In another aspect, the adjustment mechanism further includes a ratchet to control motion in one of the first rotational direction and the second rotational direction.

In yet another aspect, the adjustment mechanism further includes a ratchet to control motion in both the first rotational direction and second rotational direction.

In still another aspect, the kit further includes screws for attaching the first unit to the first bone and for attaching the second unit to the second bone.

In a further aspect, the first bone is a first vertebra and the second bone is a second vertebra.

According to yet another embodiment, the present disclosure provides a bone surgical apparatus for manipulating a curvature of a spine, the bone surgical apparatus including a unit having a first end section, a second end section fixedly coupled to the first end section, and a rotatable mechanism positioned between the first end section and the second end section, the rotatable mechanism having a first position that allows one of the first end section and the second end section to rotate in a both a first rotational direction and a second rotational direction opposed to the first rotational direction, and a second position that prevents rotation of the one of the first end section and the second end section in the second rotational direction.

The foregoing and other advantages of the invention will appear from the following description. In the description, reference is made to the accompanying drawings which form a part hereof, and in which there is shown by way of illustration a non-limiting example embodiment of the invention.

BRIEF DESCRIPTION OF THE DRAWINGS

Like reference numerals will be used to refer to like parts from Figure to Figure in the following detailed description.

DETAILED DESCRIPTION OF THE INVENTION

The present invention provides a method and apparatus that overcome the aforementioned issues by directly correcting the curve of the spine by tethering of the convexity of the curve rather than distracting the spine. The method and apparatus allow for gradual correction of the spine by providing a plurality of interconnected rods with at least a portion of the rods exhibiting a ratcheting function in order to slowly derotate the spine. In this case, the gradual correction allows the discs to adjust.

Furthermore, the method and apparatus can be used not only for correction of a growing spine but also for scoliosis or kyphosis fusion surgery. In the fusion surgery, gradual correction would allow for lower stress on the hardware involved in the procedure, potentially lowering the risk for hardware failure and therefore spinal cord injury. In addition, the present disclosure would allow for fusion of fewer levels of the spine, including patients exhibiting multiple curves where it is not uncommon to fuse a majority of the vertebrae in the thoracic and lumbar regions.

Finally, this invention can allow for correction not only during the time of the surgery but over time, after the surgery, thereby enabling gradual correction of the spinal curvature without fusion or repeated surgery, with actual correction of the curve and with less focus on distraction. Finally, by focusing on actual correction rather than distraction, this invention can allow for correction not only during the time of the surgery but also over time, after the surgery. This will thereby enable gradual correction of the spinal curvature without the need for fusion or repeated surgery.

In an example embodiment of a spinal surgical apparatus, there may be provided a bone surgical apparatus that includes a unit with a first end and an opposed second end. The first end of the unit includes a female component with an interior dimension and the second end includes a male component having an exterior dimension. The female component and the male component are capable of mating. At least one of the female and male components may also include an adjustment mechanism with a first position that allows the component to rotate in both a first rotational direction and a second rotational direction opposed to the first rotational direction, and a second position that prevents rotation of the component in the second rotational direction.

Figure 1:
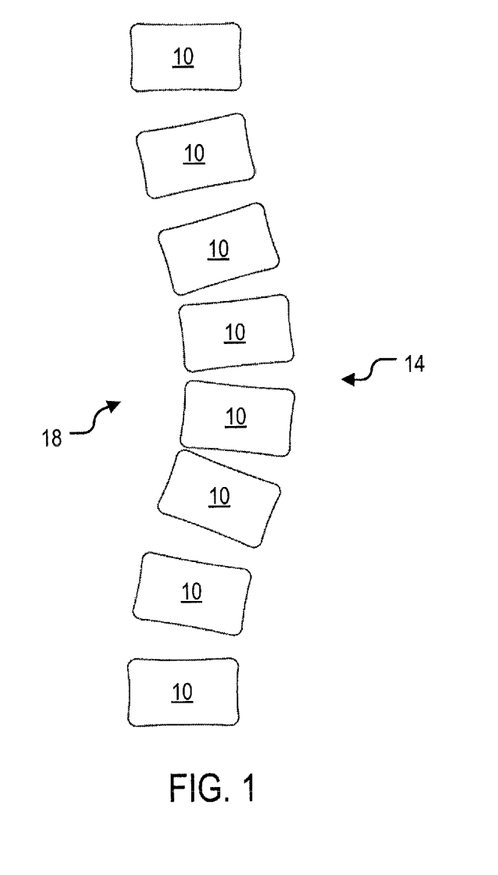
FIG. 1 illustrates schematically a scoliotic spine, viewed from the posterior.

Embodiments of the invention may further be understood with reference to the Figures. Referring to FIG. 1, an illustration is shown of the anatomical situation of a typical scoliotic spine, in which some vertebrae 10 are displaced from a normal position at least in a lateral direction. FIG. 1 is a view from the posterior, and in this illustration the vertebrae 10 are displaced to the patient's right. At the extreme of the abnormal displacement, there is, as labeled in FIG. 1, a convex portion 14 and a concave portion 18 opposed to the convex portion 14.

Figure 2:
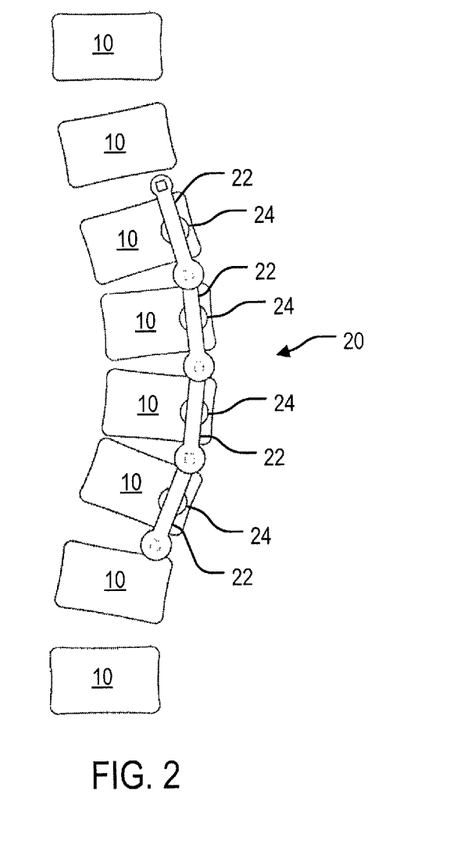
FIG. 2 is an illustration, looking at the posterior of a spine, of an apparatus of an embodiment of the invention, involving connections of the apparatus to pedicle screws, before adjustment of the apparatus.

Referring now to FIG. 2, it is illustrated that embodiments of the invention may comprise an apparatus 20 implanted along a patient's spine. FIG. 2 is an illustration prior to adjustment of the apparatus 20. In one non-limiting example, the apparatus 20 includes a plurality of linked units 22 that are coupled to the vertebrae 10 with pedicle screws 24.

Figure 3:
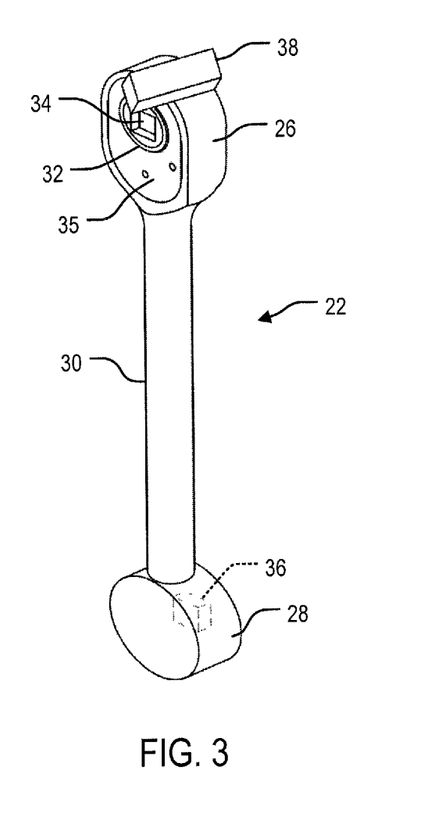
FIG. 3 is a front perspective view of a unit of the apparatus as in FIG. 2.
Figure 4:
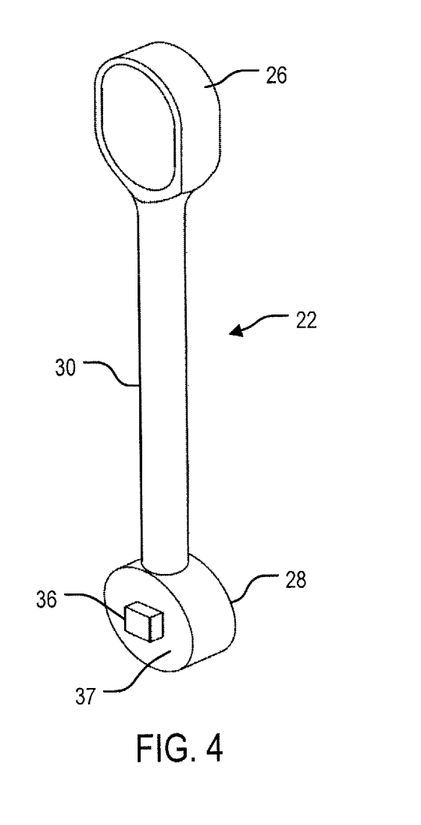
FIG. 4 is a rear perspective view of a unit of the apparatus as in FIG. 2.

Turning now to FIGS. 3 and 4, an example embodiment of a unit 22 of an apparatus 20 is shown. The unit 22 includes a first end 26 and a second end 28. The first end 26 and the second end 28 are positioned at and connected or coupled to opposing ends of a connector or cylindrical rod 30. A rotatable mechanism 32 is housed in the first end 26. In one embodiment, the rotatable mechanism 32 is an adjustable ratcheting mechanism with a receiver 34 positioned in the front face 35 of the first end 26. One example of a ratcheting mechanism that may be incorporated in an apparatus according to the present disclosure is described in U.S. Pat. No. 7,587,961 to Chiang. However, other example of ratcheting mechanisms may be incorporated into an apparatus according to the present disclosure as will be apparent to one or ordinary skill.

With continued reference to FIGS. 3 and 4, a projection 36 dimensioned to mate with the receiver 34 is positioned on a rear face 37 of the second end 28. Alternatively, the receiver 34 and the projection 36 can be positioned on the same face of the unit 22, for example both the receiver 34 and the projection 36 positioned on a front face of their respective ends. In one example, the projection 36 is a standard driver bit such as a square, hexagon, star, cross (e.g., Phillips head) or flat bit. Similarly, the receiver 34 can be shaped to receive one or more of the aforementioned driver bits such that a connection can be made between the projection 36 and the receiver 34. Also, the rod 30 may have a shape other than cylindrical. The first end 26, the rod 30, and the second end 28 may not be collinear, that is, a step off may be present between the first end 26 and the rod 30 and/or the second end 28 and the rod 30.

Furthermore, the projection 36 can include means to form a secure connection such as a reversible or irreversible lock with the receiver 34. In one aspect, the projection 36 includes a spring biased detent engageable with a feature of the receiver 34, while in another aspect, the projection can be fixedly attached to the receiver 34 such as with a pin or screw inserted through an opening in the unit 22. A secure connection ensures that the first and second units 22, 22' are also securely linked to enable suitable operation of the rotatable mechanism 32 for correction of the spine.

Figure 5:
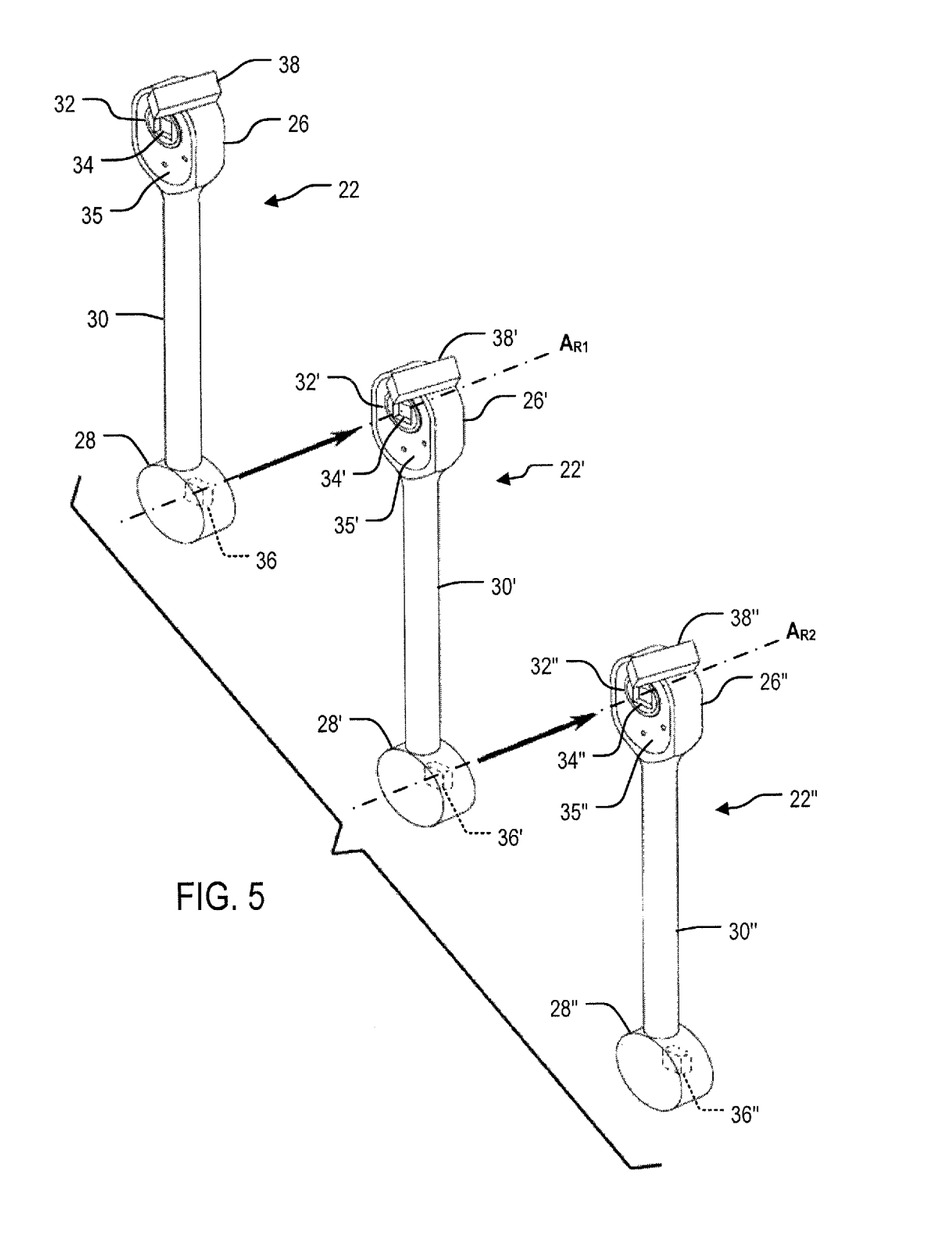
FIG. 5 illustrates an exploded perspective view of an example embodiment of a method for assembling a plurality of units as in FIG. 2 of the apparatus.

As shown in FIG. 5, a first unit 22 can be linked with a second unit 22' by mating the projection 36 on the second end 28 of the first unit 22 with the receiver 34' on the first end 26' of the second unit 22' as indicated by the arrows. Similarly, further units, such as a third unit 22", can be linked to first unit 22 and second unit 22' as illustrated in FIG. 5. In one aspect, the projection 36 located on the second end 28 of the first unit 22 can be received within the receiver 34' on the first end 26' of the second unit 22' such that the first unit 22 is rotatable relative to the second unit 22' about an axis of rotation $A_{R1}$. Similarly, the second unit 22' may be rotatable relative to the third unit 22" about an axis of rotation $A_{R2}$.

FIGS. 3-5 also illustrate an optional bumper plate 38 disposed on the first end 26 of the unit 22. In one example, the bumper plate 38 is positioned on a side of the first end 26 and projects outward from the front face 35. When a first unit 22 is linked to a second unit 22', the bumper plate 38 is configured to limit the range of motion of the first unit 22 relative to the second unit 22', and therefore the degree of rotation of the rotatable mechanism 32. Additionally (or alternatively), the rotatable mechanism 32 may include one or more internal stops (not shown) that function in a manner similar to that of the bumper plate 38. In one aspect, the angle of the bumper plate 38 or the internal stops may be adjustable or otherwise customizable. Accordingly, that the rotational motion of the first unit 22 relative to the second unit 22' (or another unit), may be specified, fixed, or otherwise controlled on a unit by unit or patient by patient basis.

Figures 6, 7:
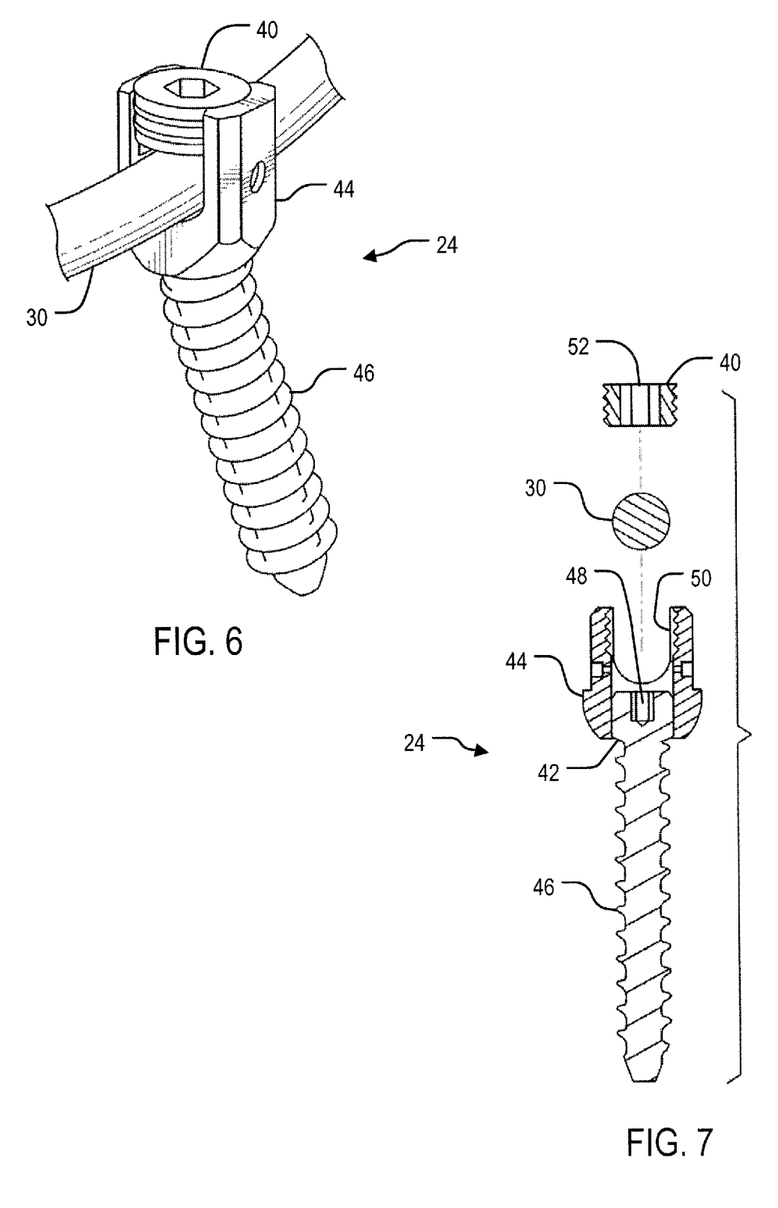
FIG. 6 is a perspective view of a pedicle screw associated with a portion of a unit as in FIG. 2 of the apparatus.
FIG. 7 is a sectional view of a pedicle screw associated with a portion of a unit as in FIG. 2 of the apparatus.

Referring to FIGS. 6 and 7, a pedicle screw 24 or other suitable fastener can couple to the cylindrical rod 30 of the unit 22 in order to couple the unit 22 to the spine. Alternatively, the cylindrical shaft 30 or another portion of the unit 22 can engage with or grip a vertebra directly. As illustrated in FIG. 2, the cylindrical rod 30 of the unit 22 is receivable in a pedicle screw 24. In one example embodiment, as shown in FIGS. 6 and 7, the pedicle screws 24 are any of the various pedicle screws known in the art. For example, a pedicle screw 24 associated with a first unit 22 can be a first type of pedicle screw, while a pedicle screw 24' associated with a second unit 22' can be a second type of pedicle screw. Similarly, other pedicle screws in the Figures that are depicted but unlabeled may optionally be any of the various pedicle screws known in the art.

FIGS. 6 and 7 shows a typical polyaxial pedicle screw 24 coupled with the cylindrical rod 30 of a unit 22. In such a pedicle screw 24, when the set screw 40 presses against the cylindrical rod 30, the cylindrical rod 30 in turn presses on the at least partially spherical screw head 42 which in turn presses the screw head 42 against the interior surface of the polyaxial head 44, thereby locking the position of the screw shaft 46 with respect to the polyaxial head 44. More particularly, this locks all of the components involved, against all degrees of freedom of motion.

With continued reference to FIGS. 6-7, the pedicle screw 24 may be installed by inserting the screw shaft 46 through the top of the polyaxial head 44 and then driving screw shaft 46 into bone utilizing recess 48. Next, the cylindrical rod 30 can be positioned in the polyaxial head 44 and the set screw 40 may then be received in threaded section 50 to thereby vertically restrain screw head 42 and polyaxial head 44. The set screw 40 can be driven into the polyaxial head 44 utilizing recess 52.

For some embodiments, as a change of position occurs in the units 22, if any of those units 22 is attached to a pedicle screw 24, it may be necessary for there to be a change in the position of the units 22 relative to the pedicle screw 24. This change may be required after the apparatus 20 has been in the patient for some time, in which situation the shaft 46 of the pedicle screw 24 may have become firmly integrated with bone. If the shaft 46 of the screw 24 is embedded immovably in bone, which is what is generally desired, then it may be necessary for some part of the remainder of the apparatus 20 to move relative to the screw shaft 46. For example, it may be necessary for part of the apparatus 20 to rotate around the axis of the screw shaft 46. If the spine is becoming generally straighter as a result of the treatment, natural growth, or both, such rotation may be desired and/or required. Therefore, in some embodiments of the apparatus 20, there may be provided a polyaxial pedicle screw 24 that permits rotation of units 22 relative to the screw shaft 46 even after the set screw 40 has been tightened so that the polyaxial head 44 firmly grasps the cylindrical rod 30.

For example, the polyaxial head 44 can be configured to form a tight fit with only the cylindrical rod 30, whereas the dimensions of the various components are chosen such that even in a tightened condition, the cylindrical rod 30 does not contact the screw head 42. This allows continued freedom of motion for all degrees of freedom associated with the seating of the screw head 42 within the polyaxial head 44. In particular, it allows rotation of the units 22 with respect to the screw shaft 46. This design provides the desired ability that after the set screw 40 has been tightened, the polyaxial head 44 is able to rotate around the lengthwise axis of the screw shaft 46. This design also allows the polyaxial head 44 to tilt in all of the various other directions with respect to the screw shaft 46 even after everything is tightened.

Yet other embodiments of the present disclosure include pedicle screws that enable essentially only one degree of freedom of motion with respect to the screw shaft, which is a more restricted form of motion. In still other embodiments, the pedicle screw comprises a screw and head formed as a monolithic component. In this case, the head is no longer polyaxial, but is rather fixed relative to the screw head and shaft. Although various structures and methods for restraining vertical movement of a polyaxial head that is separate from a screw head have been described herein, it is understood that additional or alternative structures and/or methods may be utilized in alternative embodiments.

For some embodiments of the apparatus 20, regardless of the required amount of rotation, the rotation needed would still be less than the worst angle of scoliosis. Even if the spine were perfectly straightened from its scoliotic configuration, such angular change would not be larger than the maximum angle of the scoliotic deviation of the spine prior to treatment. If the improvement to the scoliosis is less than perfect correction, then the angular change would be less.

Referring again to FIGS. 2-5, embodiments of the unit 22 comprise a first end with a rotatable mechanism 32. The rotatable mechanism 32 can allow rotation or advancement in one direction but prevent rotation or advancement in the opposite direction. Such a device may optionally be ratchetable for the described angular rotation. It is further possible that the rotatable mechanism 32 may have increments of acceptable angular positions and may have stops at those positions, such that if the unit 22 is rotated in the permitted direction, it can slip back to the nearest incremental rotational stop position and thereafter resists further rotation in the non-permitted direction. Alternatively, the rotatable mechanism 32 may be rotatable in a continuous manner, experiencing no slip-back at all.

An example ratchet device for angular rotation is illustrated in FIGS. 8-11. As illustrated, such a ratchet device may comprise a disc 60 having teeth 62 on a circumference thereof. It is possible that the teeth 62 are symmetric about a line extending along a radius of the disc 60 as shown in the Figures. It is also possible, although not necessary that the teeth 62 may have an orientation that is oriented asymmetrically with respect to a radial line so as to be oriented toward one direction of rotation and away from the opposite direction of rotation. Such a device may further comprise one or more pawls 64, 66 engageable with the teeth 62 to prevent rotation in the non-desired direction.

An operating or actuating device or control pawl device can be used to operate a post or cam or actuating member 68 received or engaged in a compartment 70 of the first end 26. The actuating member 68 can be anchored or positioned in the compartment 70 at predetermined or selected positions to selectively engage with the pawl members 64, 66 and thereby control the direction and freedom of rotation of the disc 60. In the illustrated embodiments, the pawl members 64, 66 are biased with resistance means or springs 72 towards engagement with teeth 62.

Figures 8, 9:
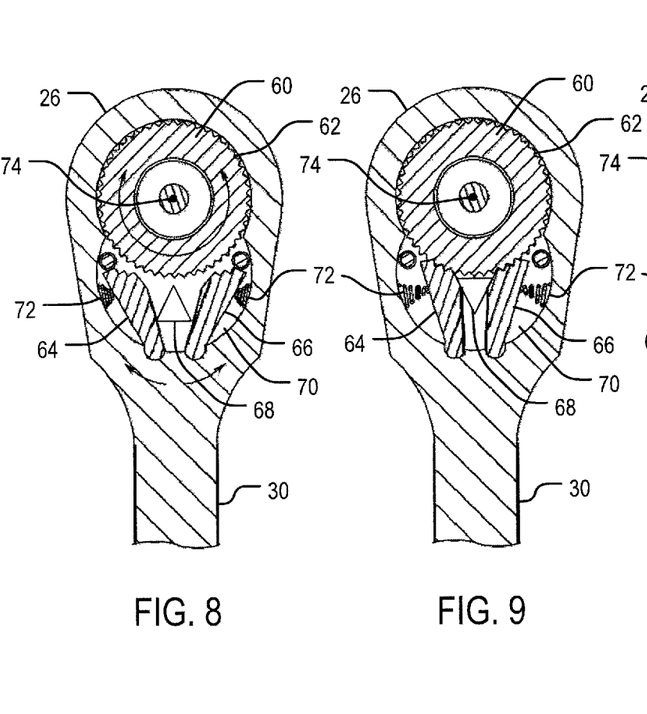
FIG. 8 is a sectional view of a free-rotation state of an example ratchet mechanism of a unit as in FIG. 2.
FIG. 9 is a sectional view of a locked state of an example ratchet mechanism of a unit as in FIG. 2.

Referring now to FIG. 8, actuating member 68 is positioned to engage with and displace both pawls 64 and 66. As a result, the pawls 64, 66 are disengaged from teeth 62 thereby allowing free rotation of the disc 60 as indicated by the arrows. Therefore, when a first unit 22 is linked with a second unit 22' as in FIG. 5, the two units 22, 22' can rotate freely relative to each other about an axis of rotation of the rotatable mechanism 32. In one aspect, the actuating member 68 may be movable by a selector (not shown) such as a handle, switch, button, or the like for enabling a user of the unit 22 to rotate or otherwise maneuver the actuating member 68.

Turning now to FIG. 9, the actuating member 68 is positioned to minimize or prevent engagement with pawls 64 and 66. As a result, the pawls 64, 66 are both biased by springs 72 to engage with teeth 62 thereby preventing rotation of the disc 60. In this position, linked units 22 and 22' are fixed in a position relative to each other.

Figures 10, 11:
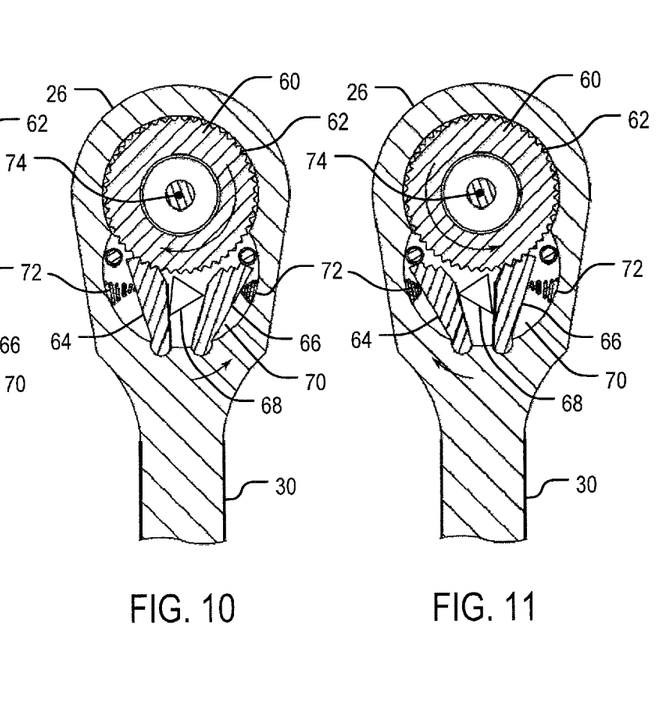
FIG. 10 is a sectional view of a clockwise rotation state of an example ratchet mechanism of a unit as in FIG. 2.
FIG. 11 is a sectional view of a counter-clockwise rotation state of an example ratchet mechanism of a unit as in FIG. 2.

FIGS. 10 and 11 illustrate the rotatable mechanism 32 in configurations in which the disc 60 is capable of either clockwise or counter-clockwise rotation, respectively. Referring first to FIG. 10, the actuating member 68 is positioned to engage with and displace pawl 66, whereas pawl 64 remains biased by spring 72 to engage with teeth 62. As a result, the pawl 66 is disengaged from teeth 62 thereby allowing rotation of the disc 60 in only the clockwise direction as indicated by the arrow. Alternatively, as shown in FIG. 11, the actuating member 68 can be positioned to only engage with pawl 64 such that pawl 64 is disengaged from teeth 62 and pawl 66 is biased by spring 72 to engage with teeth 62. This position of the actuating member 68 allows for rotation of the disc 60 in only the counter-clockwise direction as indicated by the arrow. In operation, a first unit 22 linked with a second unit 22' can rotate in either a clockwise or counter-clockwise direction about an axis of the rotatable mechanism 32 depending upon the position of the actuating member 68.

While FIGS. 8-12 illustrate one embodiment of a rotatable mechanism with a ratcheting function, alternative types of ratchet devices for angular rotation can be suitably substituted for implementation of the method and apparatus of the present disclosure. One such example of a ratchet device can comprise a disc facing another disc with teeth on the facing surfaces of one or both discs. The discs may optionally be coaxial with each other. Teeth may optionally be shaped so as to preferentially permit one direction of rotation and resist the opposite direction of rotation of the discs relative to each other. FIGS. 8-12 further illustrate a center point 74 that coincides with an axis of rotation (e.g., see AR1, AR2 in FIG. 5) of the first end 26. As described above, the first unit 22 can be linked with a second unit 22' such that the first unit 22 is rotatable relative to the second unit 22' about an axis of rotation that extends through the center point 74.

It can be noted that devices described so far (i.e., the apparatus 20) are passive mechanical devices. They do not generate any force, but rather they merely resist certain forces or motions under certain conditions and allow certain other motions under certain other conditions.

Figure 12:
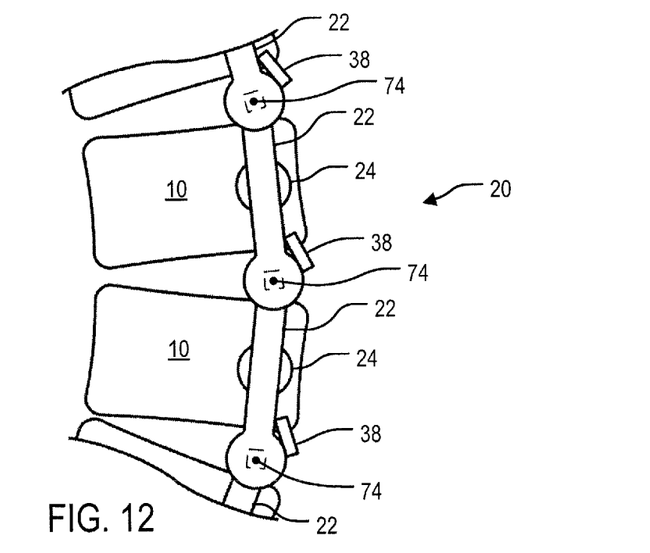
FIG. 12 is a partial illustration, looking at the posterior of a spine, of an alternative embodiment of an apparatus of the invention including bumper plates.
Figure 13:
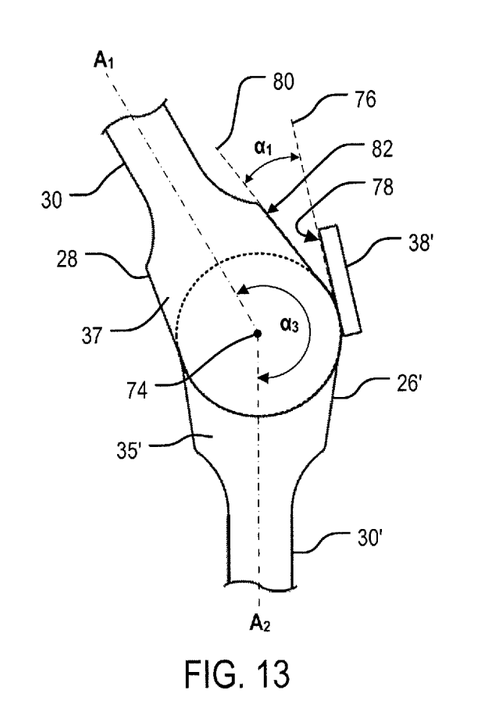
FIG. 13 is a partial front view of two coupled units of the apparatus as in FIG. 12, showing the a first unit spaced apart from a bumper plate positioned on a second unit.
Figure 14:
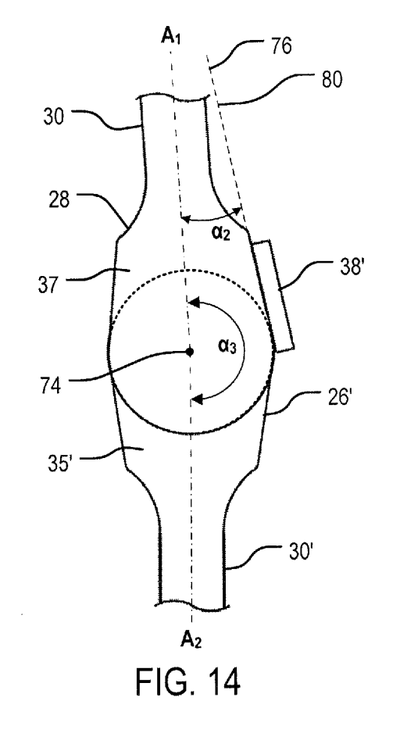
FIG. 14 is a partial front view of two coupled units of the apparatus as in FIG. 12, showing a first unit abutting a bumper plate positioned on a second unit.

Turning to FIGS. 12-14, an implementation of one example of an optional bumper plate feature is illustrated. FIG. 12 shows a partial view of an embodiment of the apparatus 20 including a number of units 22 with bumper plates 38. As in FIG. 2, the apparatus 20 in FIG. 12 is attached to the vertebrae 10 with pedicle screws 24. One advantage of the bumper plates 38 is to limit the rotation of a second end 28 of a first unit 22 relative to the first end 26 of a second unit 22' about an axis of rotation of the rotatable mechanism 32' that extends through a center point 74. As shown in FIGS. 13 and 14, the first unit 22 is capable of rotation through an angle $\alpha_1$ defined by the position of the bumper plate 38'. In particular, in FIG. 13 the first unit 22 is spaced apart from a bumper plate 38' positioned on the second unit 22'. The first unit 22 can be rotated in a clockwise direction towards the bumper plate 38' until a surface of the first unit 22 abuts the bumper plate 38' positioned on the second unit 22'. Thus, further rotation of the first unit 22 is prevented.

In one aspect, the angle $\alpha_1$ may be defined by a line 76 that extend along an inner face 78 of the bumper plate 38', and a line 80 that extends along an outer surface 82 of the second end 28. Notably, when the first unit 22 is be rotated such that the outer surface 82 of the first unit 22 abuts the inner surface 78 of the bumper plate 38' positioned on the second unit 22', the line 76 coincides with the line 80. Accordingly, the angle $\alpha_1$ is reduced to 0 degrees.

In some embodiments, the position of the bumper plate 38' may be regulated such that the angle $\alpha_1$ is 0 degrees when the body of the cylindrical rod 30 is aligned at an angle $\alpha_2$ relative to the bumper plate 38'. Additionally (or alternatively), the position of the bumper plate 38' may be regulated such that the angle $\alpha_1$ is 0 degrees when the body of the cylindrical rod 30 is aligned at an angle $\alpha_3$ relative to the body of the cylindrical rod 30'. In one aspect an axis $A_1$ is illustrated to extend generally through the center of the cylindrical rod 30 of the first unit 22 and intersect with the center point 74. Further, an axis $A_2$ is illustrated to extend generally through the center of the cylindrical rod 30' of the second unit 22' and intersect with the center point 74. The bumper plate 38' (or internal stops as described above) may be positioned or otherwise configured to achieve predefined angles $\alpha_2$ and $\alpha_3$ when the angle $\alpha_1$ is reduced to 0 degrees. Notably, the angle $\alpha_3$ may be less than, equal to, or greater than 180 degrees when the angle $\alpha_1$ is at 0 degrees. Further, there may be no angle between the axis $A_1$ and the line 76 (e.g., if the axis $A_1$ and the line 76 are parallel when $\alpha_1$ is 0 degrees.

In some embodiments, aspect, bumper plates 38 are suitably implemented where the rotatable mechanism is not fixed by engagement of either or both of the pawls 64 and 66. For example, it may be preferable to enable clockwise rotation of the first unit 22 as in FIG. 13 by positioning the actuating mechanism 68 as in FIG. 11. This arrangement would allow for a reduction in the overall curvatures of the apparatus 22 (e.g., due to correction of a curvature of the spine). However, it is also desirable to prevent over-correction or prevent individual units 22 of the apparatus 20 from over-rotating. In this case, bumper plates 38 can be positioned to prevent over-correction/rotation.

In embodiments of the present disclosure, the position of the bumper plates 38 can be fixed or adjustable. For example, the bumper plates can be fixed to unit 22 such as by welding, through the use of fasteners, or by casting unit 22 and bumper plate 38 as a monolithic structure. Alternatively, the bumper plate 38 can be adjustable relative to a unit 22. In this case, the bumper plate 38 can be adjusted and/or readjusted before, during and after a procedure based on the preference and needs of the user. Furthermore, the bumper plate 38 can have any suitable shape to be effective in limiting rotation of a unit 22.

Although the cylindrical rod 30 has been illustrated as having a both a first and second end 26, 28, that is not the only possibility. In one example, a unit 22 may lack either a first end 26 or a second end 28 such that the one end of the unit 22 terminates with the cylindrical rod 30. Units 22 without first or second ends 26, 28 are suitable, for example, for use at the termini of an apparatus 20 that includes multiple units 22. With respect to such units, alternatives to pedicle screws 24 for fastening the apparatus to the spine are possible. In some embodiments, an alternative is available given that scoliosis often involves at least partially the thoracic region of the spine. In the thoracic region, the vertebrae 10 have ribs extending laterally from them.

Accordingly, it is possible that in place of the first or second end 26, 28, the unit 22 can comprise a hook or gripping means suitable to grip a rib. Such gripping may be done near the junction between a rib and a vertebra. There may be any desired combination of an end attaching to a pedicle screw, or an end that grips a rib, or both. In embodiments of the invention that involve grasping a rib, the device may comprise any of a variety of hooks, clamps and/or other devices. It is also possible that the rib gripping means may in some embodiments be rotatable with respect to the units 22.

The units 22, as described herein, may be passive mechanical devices. Such passive mechanical devices change their configuration or dimension in the permitted direction and resist any change in the non-permitted direction, but do not actively generate force or motion and do not receive power from any external source. In other embodiments, it would be possible to use some form of motorized device for rotation. Such devices have been known to operate by transmitting an electrical or magnetic or electro-magnetic signal or coupling through the intact skin without an incision or puncture. Such a device would typically comprise a motor or some sort of actuator.

Embodiments of the invention may also include a surgical method. A non-limiting example surgical method may comprise attaching the apparatus 20 comprising a plurality of linked units 22 along the length of the spine. Such attachment may be achieved, for example, through the use of pedicle screws screwed into appropriate vertebrae. The second end 28 of a first unit 22 can be linked to the first end 26 of a second unit and the second end 28 of the second unit can be linked to the first end 26 of a third unit and so forth as illustrated in FIGS. 2 and 12. The number of units included in an apparatus 20 can vary based on the procedure and the desired outcome. While a posterior approach is illustrated herein, an anterior approach may also be used.

The cylindrical rod 30 of each unit can be coupled to a pedicle screw 24 either before or after linking to another unit 22. It is possible that a unit 22 of the apparatus 20 could involve grasping a rib using a hook, clamp, or other device, rather than attaching to a pedicle screw that is screwed into a vertebra. It is also possible that both ends of a unit 22 could involve grasping ribs. It is further possible that one portion of the unit 22 could couple to a pedicle screw and another portion could clamp around a rib. There may further be provided a variety of sizes of units 22 of the apparatus 20.

In addition to the use of an apparatus 20 in a surgical method, the method could additionally involve fusion of one or more vertebrae using techniques known in the art. For example, a method can include an autologous bone graft for lumbar fusion. Autologous bone grafts are obtained by harvesting a section of bone from the iliac crest of the patient and thereafter implanting the article of autologous bone graft to effect fusion. Alternatively, allograft bone grafts harvested from cadaveric specimens, machined, and sterilized for implantation can be used. Further methods known in the art can also be implemented, such as the use of artificial bone created in a laboratory.

It is to be understood that changes to the configuration of the apparatus 20 can be achieved during and after completion of surgery. One such change in the configuration of the units may be associated with normal growth of the patient. In regard to normal growth, embodiments of the described devices allow normal growth to occur with no increase in scoliotic deviation and possibly with some reduction of scoliotic deviation. If the various components of the spine generally grow or lengthen as a result of normal growth, the rotatable mechanisms 32 of the units 22 can undergo an angular change in the permitted angular direction, such that a general lengthening of the spine at least does not increase scoliotic deviation and may actually result in the spine becoming straighter.

Another type of change in the configuration of the apparatus 20 may involve manipulation by a physician or other treatment provider. Such treatment may be performed without surgical intervention such as puncturing of the patient's skin. For example, the patient's spine may be stretched or manipulated in such a way as to change the angular position of the units 22 relative to each other.

Moreover, manipulation so as to change the physical characteristics of the units 22 may be done periodically so as to move the spine into a closer-to-normal configuration. Such manipulation may be followed by a period of time for tissues of the patient's body to adjust and accommodate the new configuration, and potentially followed by another manipulation. Again, it is possible to perform such manipulation without puncturing or penetrating through the skin of the patient or performing any surgical procedure.

It is also possible that the apparatus can be rotated or reconfigured using surgery, which may be minimally invasive surgery. For example, during such surgery, it might only be necessary to expose a portion of the units 22. For example, it might be possible to rotate the apparatus by exposing only the mating end of a unit 22. It might not be necessary to expose or access the entire unit 22 during such surgery.

A method of use for one of the particular embodiments may be described here. In this embodiment, the apparatus 20 can be implanted in a patient, either on one side or on both sides of the spine, with cylindrical rods 30 attached to pedicle screws or to ribs in any combination. It is possible, for example, to implant an apparatus 20 on both sides of the spine if the scoliotic condition involves rotational malpositioning of the vertebrae more so than it involves lateral deformation of the spine, or if the spine is fairly flexible and deformation correction can substantially occur at the time of implantation.

Yet another possibility is that the rotatable mechanisms 32 may have a release latch that allows them to be released (i.e., freely rotated) if, for some reason, they rotate farther than desired, such as if a patient stretches or bends in such a way as to cause slippage of the member in the permitted direction but farther than is desired. For example, such a release latch could be actuated in response to an applied magnetic field. For example, if the rotatable mechanism 32 comprises a pawl, the pawl or a member associated with the pawl could be responsive to an applied magnetic field. With such an apparatus, if an appropriate magnet were brought sufficiently close to the apparatus, which could be done with the magnet outside the patient's body, the rotatable mechanism 32 could release and be able to rotate in the direction that usually is not permitted. However, the use of bumper plates 38 can in some embodiments obviate the need for such a release mechanism.

One or more of the apparatus 20 described herein may be manufactured of materials that are suitable for implantation in the human body. Many such materials are known presently. In some embodiments, one or more apparatus are made of titanium alloy, such as, for example, Ti-4Al-6Va.

While the invention has been described as a treatment for scoliosis, it is not limited to scoliosis treatment. In a condition called Scheuermann's kyphosis, the spine bends forward causing a hump in the back. The apparatus 20 is a beneficial treatment for this condition. This kyphosis can be painful and cause long term disability. Bracing is tried but final procedure would be fusion that sometimes would require front and back surgery. The apparatus 20 can be used for fusion and non-fusion treatments of kyphosis. Scheuermann's kyphosis is similar to scoliosis. Instead side to side correction as in scoliosis, the correction in Scheuermann's kyphosis would be front to back correction.

The invention may also be used in a method for fusing a first bone and a second adjacent bone. In the method, the first unit 22 of the apparatus 20 is attached to the first bone; the second unit 22' of the apparatus 20 is attached to the second bone wherein the apparatus 20 allows rotation of the first unit 22 with respect to the second unit 22' in one rotational direction but at least selectively prevents rotation in an opposed direction as described above. The first unit 22 is rotated with respect to the second unit 22' in the one rotational direction, and the first bone and the second bone to fuse, with or without the use of a bone graft that contacts the first bone and the second adjacent bone. In one non-limiting embodiment, the first bone is a first vertebrae and the second bone is a second vertebrae.

Figure 15:
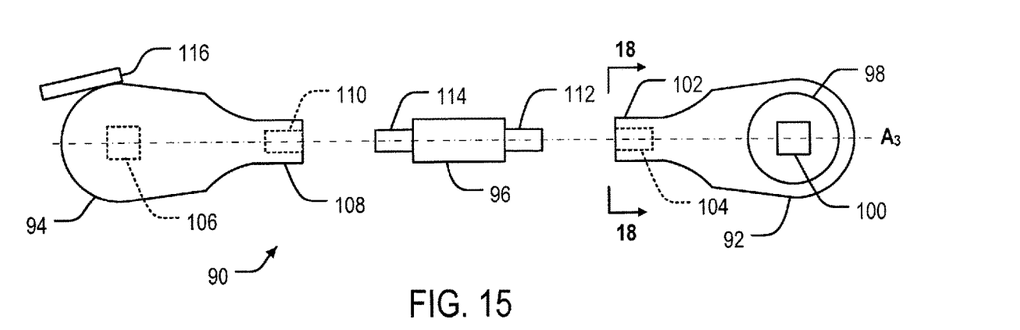
FIG. 15 is a schematic illustration of an exploded top plan view of another embodiment of an apparatus according to the present disclosure.

Turning to FIG. 15, another embodiment of the present disclosure provides a unit 90 including a first end section 92, a second end section 94, and a central connector 96. In one aspect, the first end section 92 may be similar to first end 26 as shown, for example, in FIGS. 3 and 4. For example, the first end section 92 may include a rotatable mechanism 98 and a female component or receiver 100. An end 102 of the first end section 92 can include a first end connector 104. The first end connector 104 may be a recess or bore formed within the body the of the first end section 92. The second end section 94 may be similar to second end 28 as shown, for example, in FIGS. 3 and 4. For example, the second end section 94 may include a male component or projection 106. The projection 106 may be sized to mate with the recess 100 in the first end section 92 (or a first end section of another unit). The second end section 94 may further include an end 108 having a second end connector 110. The second end connector 110 may be similar to the first end connector 104. As in the case of the apparatus 20, when a first end section 92 from one unit 90 is linked to a second end section 94 from another unit 90, the first end section 92 may be rotatable relative to the second end section 94 by way of the rotatable mechanism 98.

The central connector 96 can include a first link 112 and a second link 114. In the illustrated embodiment, the first link 112 and the second link may define cylindrical segments sized to enable to the central connector 96 to form a connection with the first end section 92 and the second end section 94. For example, the first link 112 may be sized to insert into or mate with the connector 104, while the second link 114 may be sized to insert into or mate with the connector 110. In one aspect, the connection between a link (e.g., first link 112) and a connector (e.g., connector 104) may be fixed with a set screw, an adhesive, or another like fastener. It will also be appreciated that in some embodiments, the central connector 96 may be omitted with, for example, the first end section 92 having a male component for direct connection to the connector 110. In yet other embodiments, the connector 96 may telescope, extend, or include another adjustment feature that enables the length of the connector 96 to be varied. In still other embodiments, the individual portions of the unit 90 (i.e., the first end section 92, the second end section 94 and the central connector 96) may be rotatable relative to one another about a central axis $A_3$ that extends axially through the central connector 96.

Figure 16:
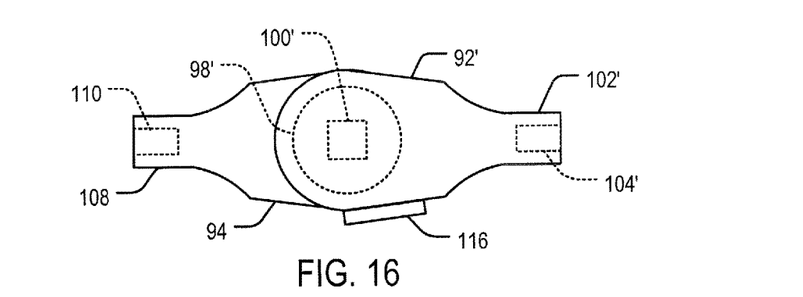
FIG. 16 is a schematic illustration of a top plan view yet another embodiment of an apparatus according to the present disclosure.
Figure 17:
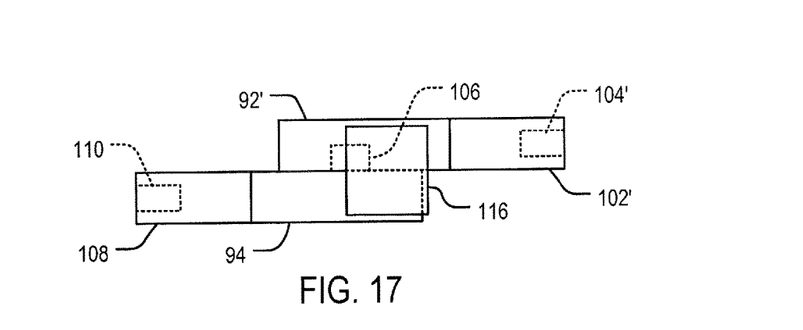
FIG. 17 is a side elevational view of the apparatus of FIG. 16.

With continued reference to FIG. 15, at least one of the first end section 92 and the second end section 94 may include a bumper plate similar to bumper plate 38 shown, at least, in FIG. 3. In the illustrated embodiment, second end section 94 includes a bumper plate 116. The bumper plate 116 may be positioned to limit rotational motion of the second end section 94 or the unit 90 in general. For example, as shown in FIGS. 16 and 17, when the second end section 94 is coupled to mate with a first end section 92' of a second unit 90', the bumper plate 116 may limit rotation of the second end section 94 of the first unit 90 relative to the first end section 92' of the second unit 90'. In some embodiments, the mated second end section 94 and first end section 92' may operate in a manner similar to the apparatus shown at least in FIGS. 13 and 14. In other embodiments, the second end section 94 and the first end section 92' may be fixed together as a single unit with the rotational motion still preserved.

Figure 18:
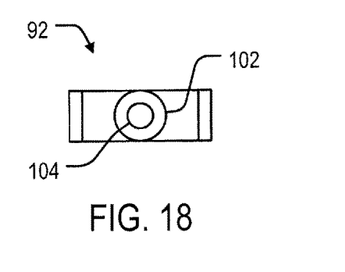
FIG. 18 is an elevational view of a portion of the apparatus of FIG. 15 as taken along the line 18-18 thereof.
Figure 19:
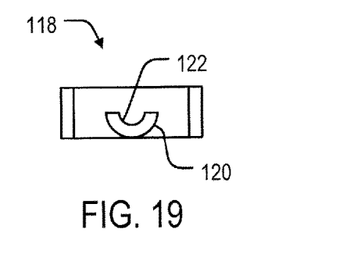
FIG. 19 is an elevational view similar to FIG. 18 showing an alternative embodiment thereof.

Turning to FIGS. 18 and 19, an end section of unit for a bone surgical apparatus may have a variety of different connectors. In one example, the first end section 92 and, more particularly, the end 102 may define a generally tubular connector 104. The connector 104 may be a female components sized to mate with a cylindrical link. With reference to FIG. 19, another embodiment of a first end unit 118 may have an end 120 that defines a generally half-cylinder or half-pipe shaped connector 122. The connector 122 may be a female components sized to mate with a cylindrical link such as the link 112. Further, each of the connector 104 and the connector 122 (or the corresponding link) may include one or more fasteners, screws, or the like to secure the resulting connection.

The invention also provides a kit for treating an abnormally shaped spine in a patient, or a kit for fusing a first bone and a second adjacent bone, such as a first and a second adjacent vertebra. The kit includes a first unit having a first end including a female component with an interior dimension; and a second unit having a second end including a male component having an exterior dimension of a mating size to the interior dimension of the female component, wherein at least one of the first unit and the second unit includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction. The kit may include fasteners, such as screws, for attaching the first unit to the first bone and for attaching the second unit to the second bone.

As used herein, the term "patient" refers to a human or non-human mammalian patient suffering from a condition in need of treatment. The present invention is generally applied to humans. In certain embodiments, non-human mammals, such as rats, may also be used for the purpose of demonstration. One may use the present invention for veterinary purpose. For example, one may wish to treat commercially important farm animals, such as cows, horses, pigs, rabbits, goats, and sheep. One may also wish to treat companion animals, such as cats and dogs.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Unless clearly indicated to the contrary, in any methods claimed herein that include more than one step or act, the order of the steps or acts of the method is not necessarily limited to the order in which the steps or acts of the method are recited.

What is claimed is:

1. A bone surgical apparatus for manipulating a curvature of a spine, the bone surgical apparatus comprising:
a unit having a first end and an opposed second end, the first end including a female component having an interior dimension, and the second end including a male component having an exterior dimension of a mating size to the interior dimension of the female component;
an adjustment mechanism having a first position that allows one of the female component and the male component to rotate in both a first rotational direction and a second rotational direction opposed to the first rotational direction, and a second position that prevents rotation of the one of the female component and the male component in the second rotational direction; and
a bumper plate positioned on one of the first end and the second end, the bumper plate being configured to limit rotation of the one of the female component and the male component with respect to one of the first end and the second end, and
wherein the bumper plate is adjustable to selectively control the rotational motion of the one of the female component and the male component with respect to the one of the first end and the second end.

2. The bone surgical apparatus of claim 1, wherein the adjustment mechanism further comprises a third position that prevents rotation of the one of the female component and the male component in both the first rotational direction and the second rotational direction.

3. The bone surgical apparatus of claim 1, wherein the adjustment mechanism further comprises a ratchet to control motion in one of the first rotational direction and the second rotational direction.

4. The bone surgical apparatus of claim 1, wherein the adjustment mechanism further comprises a ratchet to control motion in both of the first rotational direction and the second rotational direction.

5. The bone surgical apparatus of claim 1, further comprising:
a connector positioned between and coupled to the first end and the second end of the apparatus; and
a pedicle screw configured to attach to a vertebra and receive the connector.

6. The bone surgical apparatus of claim 1, further comprising a selector for selecting between the first position and the second position.

7. A kit for treating an abnormally shaped spine in a patient, the kit comprising:
a first unit having a first end including a female component with an interior dimension; and
a second unit having a second end including a male component having an exterior dimension of a mating size to the interior dimension of the female component, wherein at least one of the first unit and the second unit includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction, and wherein at least one of the first unit and the second unit includes a bumper plate positioned on one of the first end and the second end, the bumper plate being configured to limit rotation of the one of the female component and the male component with respect to one of the first end and the second end, and wherein the bumper plate is adjustable to selectively control the rotational motion of the one of the female component and the male component with respect to the one of the first end and the second end.

8. The kit of claim 7, wherein the adjustment mechanism further comprises a third position that prevents rotation of one of the female component and the male component in both the first rotational direction and the second rotational direction.

9. The kit of claim 7, wherein the adjustment mechanism further comprises a ratchet to control motion in one of the first rotational direction and the second rotational direction.

10. The kit of claim 7, wherein the adjustment mechanism further comprises a ratchet to control motion in both the first rotational direction and the second rotational direction.

11. The kit of claim 7, further comprising screws for attaching the first unit to a first vertebra and for attaching the second unit to a second vertebra.

12. A kit for fusing a first bone and a second adjacent bone in a patient, the kit comprising:

a first unit having a first end including a female component with an interior dimension; and a second unit having a second end including a male component having an exterior dimension of a mating size to the interior dimension of the female component, wherein at least one of the first unit and the second unit includes an adjustment mechanism having a first position that allows one of the female component and the male component to rotate in a both a first rotational direction and a second rotational direction opposed to the first rotational direction, and a second position that prevents rotation of the one of the female component and the male component in the second rotational direction, and wherein at least one of the first unit and the second unit includes a bumper plate positioned on one of the first end and the second end, the bumper plate being configured to limit rotation of the one of the female component and the male component with respect to one of the first end and the second end, and wherein the bumper plate is adjustable to selectively control the rotational motion of the one of the female component and the male component with respect to the one of the first end and the second end.

13. The kit of claim 12, wherein the adjustment mechanism further comprises a third position that prevents rotation of one of the female component and the male component in both the first rotational direction and the second rotational direction.

14. The kit of claim 12, wherein the adjustment mechanism further comprises a ratchet to control motion in one of the first rotational direction and the second rotational direction.

15. The kit of claim 12, wherein the adjustment mechanism further comprises a ratchet to control motion in both the first rotational direction and second rotational direction.

16. The kit of claim 12, further comprising screws for attaching the first unit to the first bone and for attaching the second unit to the second bone.

17. The kit of claim 12, wherein the first bone is a first vertebra and the second bone is a second vertebra.

18. A bone surgical apparatus for manipulating a curvature of a spine, the bone surgical apparatus comprising:

a unit having a first end section, a second end section fixedly coupled to the first end section, and a rotatable mechanism positioned between the first end section and the second end section, the rotatable mechanism having a first position that allows one of the first end section and the second end section to rotate in both a first rotational direction and a second rotational direction opposed to the first rotational direction, and a second position that prevents rotation of the one of the first end section and the second end section in the second rotational direction, and wherein the unit includes a bumper plate positioned on one of the first end section and the second end section, the bumper plate being configured to limit rotation of the one of the first end section and the second end section with respect to the other of the first end section and the second end section, and wherein the bumper plate is adjustable to selectively control the rotational motion of the one of the first end section and the second end section with respect to the other of the first end section and the second end section.

* * * * *